United States Patent
Chian et al.

(10) Patent No.: US 11,399,723 B2
(45) Date of Patent: Aug. 2, 2022

(54) NON-CONTACT METHOD OF PHYSIOLOGICAL CHARACTERISTIC DETECTION

(71) Applicant: NATIONAL SUN YAT-SEN UNIVERSITY, Kaohsiung (TW)

(72) Inventors: De-Ming Chian, Kaohsiung (TW); Chao-Kai Wen, Kaohsiung (TW)

(73) Assignee: NATIONAL SUN YAT-SEN UNIVERSITY, Kaohsiung (TW)

(*) Notice: Subject to any disclaimer, the term of this patent is extended or adjusted under 35 U.S.C. 154(b) by 477 days.

(21) Appl. No.: 16/718,258

(22) Filed: Dec. 18, 2019

(65) Prior Publication Data

US 2021/0121075 A1 Apr. 29, 2021

(30) Foreign Application Priority Data

Oct. 23, 2019 (TW) ................................ 108138265

(51) Int. Cl.
*A61B 5/0205* (2006.01)
*G01S 13/88* (2006.01)

(52) U.S. Cl.
CPC ............ *A61B 5/0205* (2013.01); *G01S 13/88* (2013.01)

(58) Field of Classification Search
CPC ... A61B 5/0205; A61B 5/0507; A61B 5/0816; A61B 5/7257; G01S 13/88; G01S 7/415; G01S 13/34
See application file for complete search history.

(56) References Cited

U.S. PATENT DOCUMENTS 10,413,210 B2 * 9/2019 Horng ................ A61B 5/0002
2015/0223701 A1 * 8/2015 Ghaemi ................ A61B 5/725
600/407

FOREIGN PATENT DOCUMENTS

CN 106901695 B 8/2019

* cited by examiner

*Primary Examiner* — Omeed Alizada
(74) *Attorney, Agent, or Firm* — WPAT, PC

(57) ABSTRACT

A non-contact method of physiological characteristic detection is provided to reduce the time consumption and complexity in calculation. The method includes transmitting a radar signal to at least one detected object through radar to obtain a reflected signal lasting for at least one time session, setting an estimated frequency for each of the at least one time session, obtaining a wave energy corresponding to the estimated frequency, and converging the wave energy with respect to the reflected signal through an optimized algorithm to obtain a physiological characteristic of the at least one detected object.

19 Claims, 4 Drawing Sheets

NON-CONTACT METHOD OF PHYSIOLOGICAL CHARACTERISTIC DETECTION

CROSS REFERENCE TO RELATED APPLICATION

The application claims the benefit of Taiwan application serial No. 108138265, filed on Oct. 23, 2019, and the entire contents of which are incorporated herein by reference.

BACKGROUND OF THE INVENTION

1. Field of the Invention

The present invention relates to a detection method, in particular to a method for detecting physiological characteristic by using radar.

2. Description of the Related Art

As one of the important physiological characteristics of human body, respiration and heart rate can be directly used to reflect the physiological state of human respiratory and circulatory systems. Medical care personnel usually obtain the respiratory value or heart rate value of human body through measurement as the judgment parameter of human physiological state. In medical treatment, it is an important basis for clinical diagnosis and disease prevention.

The conventional method of physiological characteristic detection is divided into two types: contact type and non-contact type. The non-contact type detection method is capable of transmitting a radar signal to a human body through radar, and extracting the physiological characteristic of the human body according to the reflected signal of the radar signal. However, in performing signal processing on the reflected signal, Fourier transform must be performed on the reflected signal, and the reflected signal is converted from the time domain to the frequency domain to obtain the physiological characteristic such as respiration or heart rate, resulting in computational complexity and time consuming problems of the conventional method of physiological characteristic detection.

Referring to FIG. 1, the conventional method of physiological characteristic detection aims at observing the change of physiological characteristics in a short time. For example, the time session is set as 5 seconds (the corresponding frequency resolution is 0.2 Hz), and the actual respiratory frequency of the subject is 0.3 Hz in this time session. The conventional method of physiological characteristic detection is to perform Fourier transform on the reflected signal, such that it can only calculate the respiratory frequencies of 0 Hz, 0.2 Hz, 0.4 Hz, 0.6 Hz and 0.8 Hz as limited by the frequency resolution. Therefore, if the peak value in frequency domain is taken as the respiratory frequency of the subject, the respiratory frequency of the subject can be obtained as 0.4 Hz (as shown in the curve in FIG. 1). However, the error between the actual respiratory frequency and the respiratory frequency detected by the conventional method of physiological characteristic detection is 6 per minute. Therefore, the conventional method of physiological characteristic detection that obtains the physiological characteristic of the subject through the Fourier transform results is subject to the limit of frequency resolution.

In view of this, it is necessary to improve the conventional method of physiological characteristic detection.

SUMMARY OF THE INVENTION

In order to solve the above problems, the objective of the present invention is to provide a non-contact method of physiological characteristic detection capable of accurately detecting the physiological characteristic of the detected object without being affected by the frequency resolution.

A second objective of the present invention is to provide a non-contact method of physiological characteristic detection capable of obtaining physiological characteristics through signal processing without the need to go through complex computer operations.

The other objective of the present invention is to provide a non-contact method of physiological characteristic detection capable of simultaneously detecting and tracking a plurality of physiological characteristics.

The quantifiers of "a" or "one" are used for the elements and components recorded in the full text of the invention only for the convenience of use and are to provide the general meaning of the scope of the invention. In the invention, they shall be interpreted as including one or at least one, and the single concept also includes the plural, unless otherwise clearly indicated.

The non-contact method of physiological characteristic detection of the invention comprises: transmitting a radar signal to at least one detected object through radar to obtain a reflected signal lasting for at least one time session; setting an estimated frequency for each of the at least one time session; obtaining a wave energy corresponding to the estimated frequency; and converging the wave energy with respect to the reflected signal through an optimized algorithm to obtain a physiological characteristic of each of the at least one detected object.

Furthermore, the non-contact method of physiological characteristic detection of the invention comprises: transmitting a radar signal to at least one detected object through radar to obtain a reflected signal lasting for at least one time session; performing a pre-processing procedure on the reflected signal that is configured to set an estimated frequency relative to the at least one time session to obtain a wave energy corresponding to the estimated frequency, making the wave energy converge with respect to the reflected signal through an optimized algorithm to obtain a distance characteristic of each of the at least one detected object, tracking the distance characteristic of each of the at least one detected object in the at least one time session, obtaining a distance change function of each of the at least one detected object according to a change of the distance characteristic in each of the at least one time session; converting the distance change function to the frequency domain to generate spectrum information of the distance change function, and obtaining a physiological characteristic of each of the at least one detected object according to the spectrum information.

Furthermore, the non-contact method of physiological characteristic detection of the invention comprises: transmitting a radar signal to at least one detected object through radar to obtain a reflected signal lasting for at least one time session; performing a pre-processing procedure on the reflected signal that is configured to set a first estimated frequency for each of the at least one time session to obtain a wave energy corresponding to the first estimated frequency, making the wave energy converge with respect to the reflected signal through an optimized algorithm to obtain a distance characteristic of each of the at least one detected object, tracking the distance characteristic of each of the at least one detected object in the at least one time session, obtaining a distance change function of the at least one detected object according to a change of the distance characteristic in each of the at least one time session; setting a second estimated frequency for each of the at least one time session to obtain a wave energy corresponding to the second estimated frequency, and making the wave energy of the second estimated frequency converge relative to the distance change function through the optimized algorithm to obtain a physiological characteristic of each of the at least one detected object.

Accordingly, the non-contact method of physiological characteristic detection of the invention is capable of converging the wave energy of the set estimated frequency with respect to the reflected signal of the radar through an optimized algorithm to obtain the physiological characteristic of the subject. In this way, the non-contact method of physiological characteristic detection of the present invention can reflect the change of the physiological characteristic of the subject in a short time without being affected by the frequency resolution, and has the effect of improving the accuracy of detecting the physiological characteristic.

The estimated frequency is any frequency in a fundamental frequency band corresponding to a physiological characteristic signal, or a frequency having a maximum peak value in spectrum information generated by converting the reflected signal to frequency domain. In this way, the physiological characteristic can be calculated without converting the acquired reflected signal to the frequency domain or reducing at least one round of conversion process converting the reflected signal to the frequency domain, thereby reducing the calculation complexity and improving the operational efficiency.

When a number of the at least one detected object is plural, it is determined whether a number of the physiological characteristics obtained in each of the at least one time session is less than a number of the plurality of detected objects, wherein, if the determined result is positive, the method further comprises: calculating a signal difference between the reflected signal and a wave corresponding to the physiological characteristic to generate a residual signal, reselecting any frequency in the fundamental frequency band as the estimated frequency or selecting a frequency having a maximum peak value from the spectrum information of the residual signal as the estimated frequency, and performing an optimized algorithm to converge the wave energy of the estimated frequency relative to the residual signal to obtain the physiological characteristic of another of the plurality of detected objects. In this way, it has the effect of simultaneously detecting the physiological characteristics of several persons.

When the at least one time session includes a plurality of time sessions, the physiological characteristic(s) obtained in a first time session of the plurality of time sessions is taken as the estimated frequency of a second time session of the plurality of time sessions succeeding the first time session. In this way, it has the effect of simultaneously tracking the physiological characteristics of several persons in different time sessions.

When a number of the at least one time session includes a plurality of time sessions, the physiological characteristic(s) of the at least one detected object calculated in each of the plurality of time sessions is sorted by energy. The physiological characteristic(s) equal to the number of the at least one detected object is selected in order by way of energy selection from large to small. The physiological characteristics with the same order in the plurality of time sessions are taken as the physiological characteristics of the same one of the at least one detected object. In this way, it has the effect of simultaneously tracking the physiological characteristics of several persons in different time sessions.

The estimated frequency is any frequency in a fundamental frequency band corresponding to a distance characteristic signal, or a frequency having a maximum peak value in the spectrum information generated by converting the reflected signal to the frequency domain. In this way, the physiological characteristic can be calculated without converting the acquired reflected signal to the frequency domain or reducing at least one round of conversion process converting the reflected signal to the frequency domain, thereby reducing the calculation complexity and improving the operational efficiency.

When the at least one detected object includes a plurality of detected objects, the method further comprises determining whether a number of the distance characteristic(s) obtained in each of the at least one time session is less than a number of the plurality of detected objects. If the determined result is positive, the method further comprises calculating a signal difference between the reflected signal and a wave corresponding to the distance characteristic to generate a residual signal, reselecting any frequency in the fundamental frequency band as the estimated frequency or selecting a frequency having a maximum peak value from the spectrum information of the residual signal as the estimated frequency, performing the optimized algorithm to converge the wave energy of the estimated frequency relative to the residual signal through the optimized algorithm to obtain the distance characteristic of another of the plurality of detected objects, and obtaining the physiological characteristic of the other of the plurality of detected objects according to the distance characteristic. In this way, it has the effect of simultaneously detecting the distance characteristics of several persons containing the physiological characteristics.

When the at least one time session includes a plurality of time sessions, the distance characteristic of the distance change function of each of the at least one detected object in a first time session of the plurality of time sessions is taken as the estimated frequency of a second time session of the plurality of time sessions succeeding the first time session. In this way, the number of the signal processing operations, such as Fourier transform, can be reduced in the calculation process of obtaining the distance characteristics. It has the effects of simultaneously tracking several persons in different time sessions, containing the distance characteristic of the physiological characteristic, and reducing the calculation complexity and improving the operational efficiency.

When the at least one time session includes a plurality of time sessions, the distance characteristic(s) calculated in each of the plurality of time sessions is sorted by energy. The distance characteristic(s) equal to a number of the at least one detected object is selected in order by way of energy selection from large to small. The distance characteristics with a same order in the plurality of time sessions are taken as the distance characteristics of a same one of the at least one detected object to thereby generate the distance change function of the same one of the at least one detected object in the plurality of time sessions. In this way, the number of signal processing operations, such as Fourier transform, can be reduced in the calculation process of obtaining the distance characteristic. It has the effects of simultaneously tracking several persons in different time sessions, containing the distance characteristic of the physiological characteristic, and reducing the calculation complexity and improving the operational efficiency.

The estimated frequency is any frequency in a fundamental frequency band corresponding to a distance characteristic signal, or a frequency having a maximum peak value in the spectrum information generated by converting the reflected signal to the frequency domain. In this way, the physiological characteristic can be calculated without converting the acquired reflected signal to the frequency domain or reducing at least one round of conversion process converting the reflected signal to the frequency domain, thereby reducing the calculation complexity and improving the operational efficiency.

When the at least one detected object includes a plurality of detected objects, the method further comprises determining whether a number of the distance characteristic obtained in each of the at least one time session is less than a number of the plurality of detected objects. If the determined result is positive, the method further comprises: calculating a signal difference between the reflected signal and a wave corresponding to the distance characteristic to generate a residual signal, reselecting any frequency in the fundamental frequency band as the estimated frequency or selecting a frequency having a maximum peak value from the spectrum information of the residual signal as the estimated frequency, performing the optimized algorithm to converge the wave energy of the estimated frequency relative to the residual signal to obtain the distance characteristic of another of the plurality of detected objects, and obtaining the physiological characteristic of the other of the plurality of detected objects according to the distance characteristic. In this way, it has the effect of simultaneously detecting the distance characteristics of several persons containing the physiological characteristics.

The second estimated frequency is any frequency in a fundamental frequency band corresponding to a physiological characteristic signal, or a frequency having a maximum peak value in spectrum information generated by converting the distance change function to the frequency domain. In this way, the physiological characteristic can be calculated without converting the acquired reflected signal to the frequency domain or reducing at least one round of conversion process converting the reflected signal to the frequency domain, thereby reducing the calculation complexity and improving the operational efficiency.

When the at least one detected object includes a plurality of detected objects, the method further comprises determining whether a number of the physiological characteristic obtained in each of the at least one time session is less than a number of the plurality of detected objects. If the determined result is positive, the method further comprises calculating a signal difference between the distance change function and a wave corresponding to the physiological characteristic to generate a residual signal, reselecting any frequency in the fundamental frequency band as the second estimated frequency or selecting a frequency having a maximum peak value from the spectrum information of the residual signal as the second estimated frequency, performing the optimized algorithm to converge the wave energy of the second estimated frequency relative to the residual signal to obtain the physiological characteristic of another of the plurality of detected objects. In this way, it has the effect of simultaneously detecting the physiological characteristics of several persons.

When the at least one time session includes a plurality of time sessions, the distance characteristic of the distance change function of each of the at least one detected object in a first time session of the plurality of time sessions is taken as the first estimated frequency of a second time session of the plurality of time sessions succeeding the first time session. In this way, the number of signal processing operations, such as Fourier transform, can be reduced in the calculation process of obtaining the distance characteristic. It has the effects of simultaneously tracking several persons in different time sessions, containing the distance characteristic of the physiological characteristic, and reducing the calculation complexity and improving the operational efficiency.

When the at least one time session includes a plurality of time sessions, the distance characteristic(s) calculated in each of the plurality of time sessions is sorted by energy. The distance characteristics equal to a number of the at least one detected object is selected in order by way of energy selection from large to small. The distance characteristics with a same order in the plurality of time sessions are taken as the distance characteristics of a same one of the at least one detected object to thereby generate the distance change function of the same one of the at least one detected object in the plurality of time sessions. In this way, the number of signal processing operations, such as Fourier transform, can be reduced in the calculation process of obtaining the distance characteristic. It has the effects of simultaneously tracking several persons in different time sessions, containing the distance characteristic of the physiological characteristic, and reducing the calculation complexity and improving the operational efficiency.

When the at least one time session includes a plurality of time sessions, the physiological characteristic obtained in a first time session of the plurality of time sessions is taken as the second estimated frequency of a second time session of the plurality of time sessions succeeding the first time session. In this way, it has the effect of simultaneously tracking the physiological characteristics of several persons in different time sessions.

When the at least one time session includes a plurality of time sessions, the physiological characteristic(s) calculated in each of the plurality of time sessions is sorted by energy. The physiological characteristic(s) equal to a number of the at least one detected object is selected in order by way of energy selection from large to small. The physiological characteristics with a same order in the plurality of time sessions are taken as the physiological characteristics of a same one of the at least one detected object. In this way, it has the effect of simultaneously tracking the physiological characteristics of several persons in different time sessions.

BRIEF DESCRIPTION OF THE DRAWINGS

The present invention will become more fully understood from the detailed description given hereinafter and the accompanying drawings which are given by way of illustration only, and thus are not limitative of the present invention, and wherein.

DETAILED DESCRIPTION OF THE INVENTION

Figure 1:
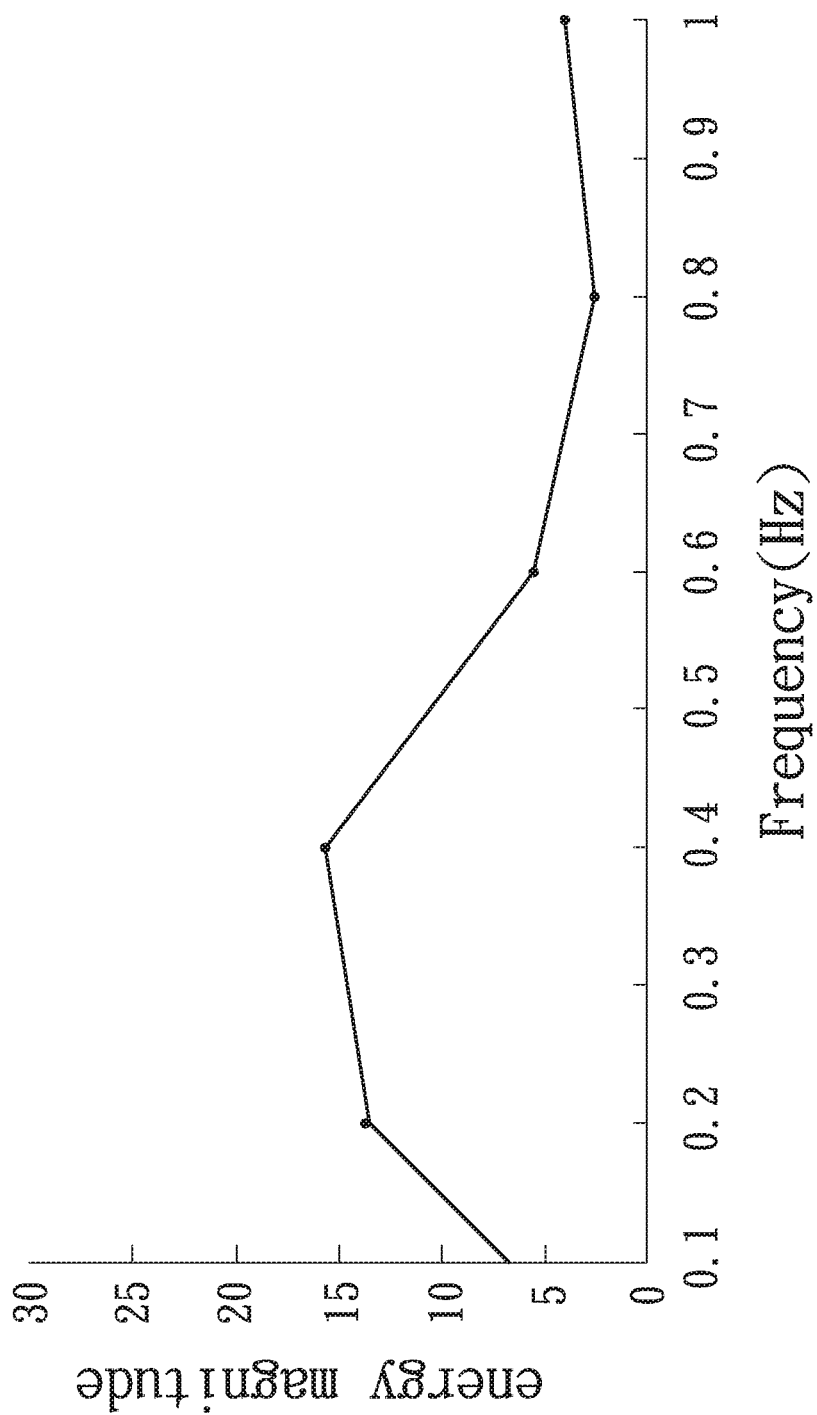
FIG. 1 is a diagram showing an energy frequency relationship of a physiological characteristic of a conventional method of physiological characteristic detection.
Figure 2:
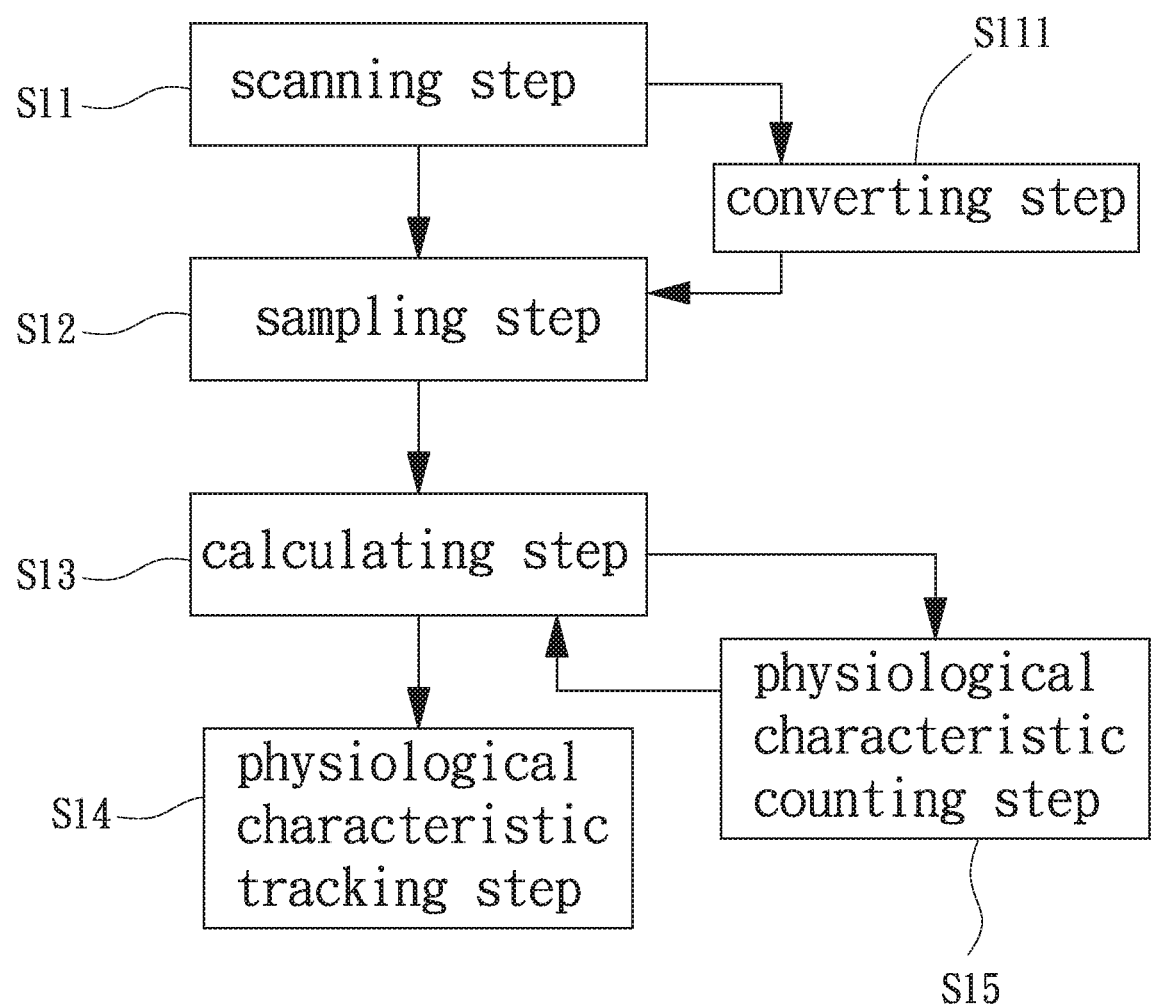
FIG. 2 is a method flow chart of a first embodiment of the present invention.

In order to make the above and other purposes, features and advantages of the present invention more obvious and understandable, the preferred embodiments of the present invention are hereinafter highlighted and illustrated in detail with the accompanying drawings as follows:

Referring to FIG. 2, a first embodiment of the non-contact method of physiological characteristic detection of the present invention includes a scanning step S11, a sampling step S12 and a calculating step S13.

The scanning step S11 is configured to transmit a radar signal to at least one detected object (such as a person or an animal) through radar to obtain a reflected signal lasting for at least one time session. The number of the radar(s) is not limited in the invention. In this embodiment, the number of the radar is described as one. The reflected signal can be a single signal or a mixed signal. In this embodiment, the radar signal transmitted by the radar can be a single-frequency continuous wave (CW) or a frequency-modulated continuous wave (FMCW). When the radar signal is the frequency-modulated continuous wave, the frequency modulation can be carried out with a triangular wave, a saw tooth wave, or by way of coded frequency modulation or noise frequency modulation, but is not limited thereto.

Specifically, the radar can continuously transmit a radar signal for a period of detection time to the detected object, and the detection time can include the at least one time session. When the at least one time session includes a plurality of time sessions, the time sessions can be sequentially divided into a first time session, a second time session, a third time session, etc. The length of each time session can be equal or unequal, which is not taken as a limited sense. In this embodiment, the detection time can be set to 30 seconds, and the first time session can be set to 1-15 seconds; the second time session can be set to 2-16 seconds or 3-17 seconds. When the second time session is set to 2-16 seconds, the third time session can be set to 3-30 seconds. The frequency of the radar signal can be an electromagnetic wave of 2.45 GHz in the S band. It is worth mentioning that when the radar scans the detected object, the detected object preferably remains in the same motion state such that the reflected signal does not change greatly, thereby improving the accuracy of signal judgment.

The sampling step S12 is configured to set an estimated frequency for the time session. Specifically, the estimated frequency can be any frequency in the fundamental frequency band corresponding to a physiological characteristic signal, or can be obtained by performing a converting step S111. Specifically, when the physiological characteristic signal is a respiratory signal, the estimated frequency is preferably set to any frequency in the fundamental frequency band, which is, for example, 0.5 Hz, as it can be understood by those with ordinary skill in the art. On the other hand, the converting step S111 can convert the reflected signal to the frequency domain through discrete Fourier transform (DFT) or fast Fourier transform (FFT) to generate spectrum information of the reflected signal. The sampling step S12 can take the frequency having a maximum peak value in the spectrum information as the estimated frequency.

It is worth mentioning that when the number of the at least one detected object is one and the number of the at least one time session is also one, the sampling step S12 can select any frequency in the fundamental frequency band as the estimated frequency. Further, when the number of the at least one detected object is one and the number of the at least one time session is plural, the sampling step S12 arbitrarily selects at least one time session in the plural time sessions, and takes any frequency in the fundamental frequency band as the estimated frequency of the detected object in the time session. Furthermore, when the number of the at least one detected object is plural and the number of the at least one time session is one, the sampling step S12 arbitrarily selects at least one detected object in the plural detected objects, and takes any frequency in the fundamental frequency band as the estimated frequency of the detected object. Moreover, when the number of the at least one detected object is plural and the number of the at least one time session is also plural, the sampling step S12 can arbitrarily select at least one time session in the plural time sessions, arbitrarily select at least one detected object in the plural detected objects in the time session, and take any frequency in the fundamental frequency band as the estimated frequency of the detected object. In this way, the present invention does not need to perform Fourier transform calculations in the calculation process of detecting the physiological characteristics, or can reduce at least one round of Fourier transform calculations, which has the functions of reducing the calculation complexity and improving the operational efficiency.

The calculating step S13 is configured to obtain the energy of the wave corresponding to the estimated frequency. The wave can be a sinusoidal wave, a square wave or a triangular wave, but is not limited thereto. The calculating step S13 is performed by an optimized algorithm to converge the wave energy with respect to the reflected signal, which is to optimize the wave energy to minimize the energy difference corresponding to the reflected signal, so as to obtain a physiological characteristic of the detected object. In this embodiment, the optimized algorithm can be gradient descent method or Newton method.

The first embodiment of the non-contact method of physiological characteristic detection of the invention can further include a physiological characteristic tracking step S14, which is configured to track the physiological characteristics of the plural detected objects in each time session. For example, when the number of the at least one time session is plural, the physiological characteristics acquired in a first time session of the plural time sessions can be used as an estimated frequency of a second time session of the plural time sessions succeeding the first time session. That is, the physiological characteristic of the previous time session is used as the estimated frequency of the next time session. Specifically, when the physiological characteristics of the detected object is acquired in the second time session, the sampling step S12 can take the physiological characteristics calculated in the first time session as the estimated frequency of the second time session. The calculating step S13 obtains the energy of the wave corresponding to the estimated frequency of the second time session, and converges the wave energy with respect to the reflected signal of the second time session through the optimized algorithm, so as to minimize the energy difference between the wave energy corresponding to the estimated frequency and the reflected signal to obtain the physiological characteristic of the detected object in the second time session.

On the other hand, when the physiological characteristics of plural detected objects are obtained in the first time session and the second time session, the physiological characteristic tracking step S14 can, in addition to using the above method to track the physiological characteristics of the plural detected objects in each time session, can also track the physiological characteristics of the plural detected objects in each time session by sorting the energy intensities corresponding to the physiological characteristics obtained in the first time session and the second time session. The energy intensities can be sorted from large to small or from small to large, which is not used to limit the present invention.

Specifically, the physiological characteristic tracking step S14 can perform energy sorting on the calculated physiological characteristics in each time session, and sequentially select the physiological characteristics equivalent to the number of the at least one detected object by way of energy selection from large to small. In this regard, the physiological characteristics having the same sorting order in each time session are taken as the physiological characteristics of the same detected object. For example, the physiological characteristics having the maximum energy in the first time session and the second time session are physiological characteristics of one of the plural detected objects; the physiological characteristics having the second largest energy in the first time session and the second time session are physiological characteristics of another detected object, and so on.

The first embodiment of the non-contact method of physiological characteristic detection of the invention can further include a physiological characteristic counting step S15, which is configured to determine whether the number of the physiological characteristic obtained in each time session is less than the number of the at least one detected object when the number of the at least one detected object is plural. If the determined result is yes, the signal difference between the reflected signal and the wave corresponding to the physiological characteristic can be calculated to generate a residual signal. In this regard, a frequency can be selected from the fundamental frequency band as the estimated frequency or the frequency having the maximum peak value can be selected from the spectrum information of the residual signal as the estimated frequency. The calculating step S13 uses the optimized algorithm to converge the wave energy of the estimated frequency with respect to the residual signal to obtain a physiological characteristic of another detected object. If the determined result is no, it means that the number of the physiological characteristic(s) that meets the physiological characteristic(s) of the at least one detected object has been obtained, then the physiological characteristic counting step S15 can be stopped.

When the respiratory frequencies of the two subjects are detected at the same time, assuming that the reflected signals have a respiratory signal of 0.3 Hz and 0.7 Hz and that the frequency resolution is 0.2 Hz; in this regard, the non-contact method of physiological characteristic detection according to the first embodiment of the invention is applied when the estimated frequency of the first time session is set to 0.5 Hz. In this situation, since the energy corresponding to 0.3 Hz respiratory signal is relatively large, the wave energy corresponding to the estimated frequency will gradually converge toward 0.3 Hz when the optimized algorithm is performed on the estimated frequency, so as to obtain the respiratory frequency of one of the two subjects as 0.3 Hz. Since the number of the respiratory frequencies currently obtained is less than the number of the subjects, an estimated frequency is reset and the signal difference between the reflected signal and the wave corresponding to the respiratory frequency is calculated to generate a residual signal. Assuming that the estimated frequency is still set to 0.5 Hz, after performing the optimized algorithm on the estimated frequency, since only 0.7 Hz respiratory signal remains in the reflected signal, the wave energy corresponding to the estimated frequency will gradually converge toward 0.7 Hz, so as to obtain the respiratory frequency of the other of the two subjects as 0.7 Hz. Subsequently, if it is necessary to detect and obtain the respiratory frequencies of the two subjects in the second time session, 0.3 Hz and 0.7 Hz can be used as the estimated frequencies of the second time session to obtain the respiratory frequencies of the two subjects in the second time session, respectively.

Figure 3:
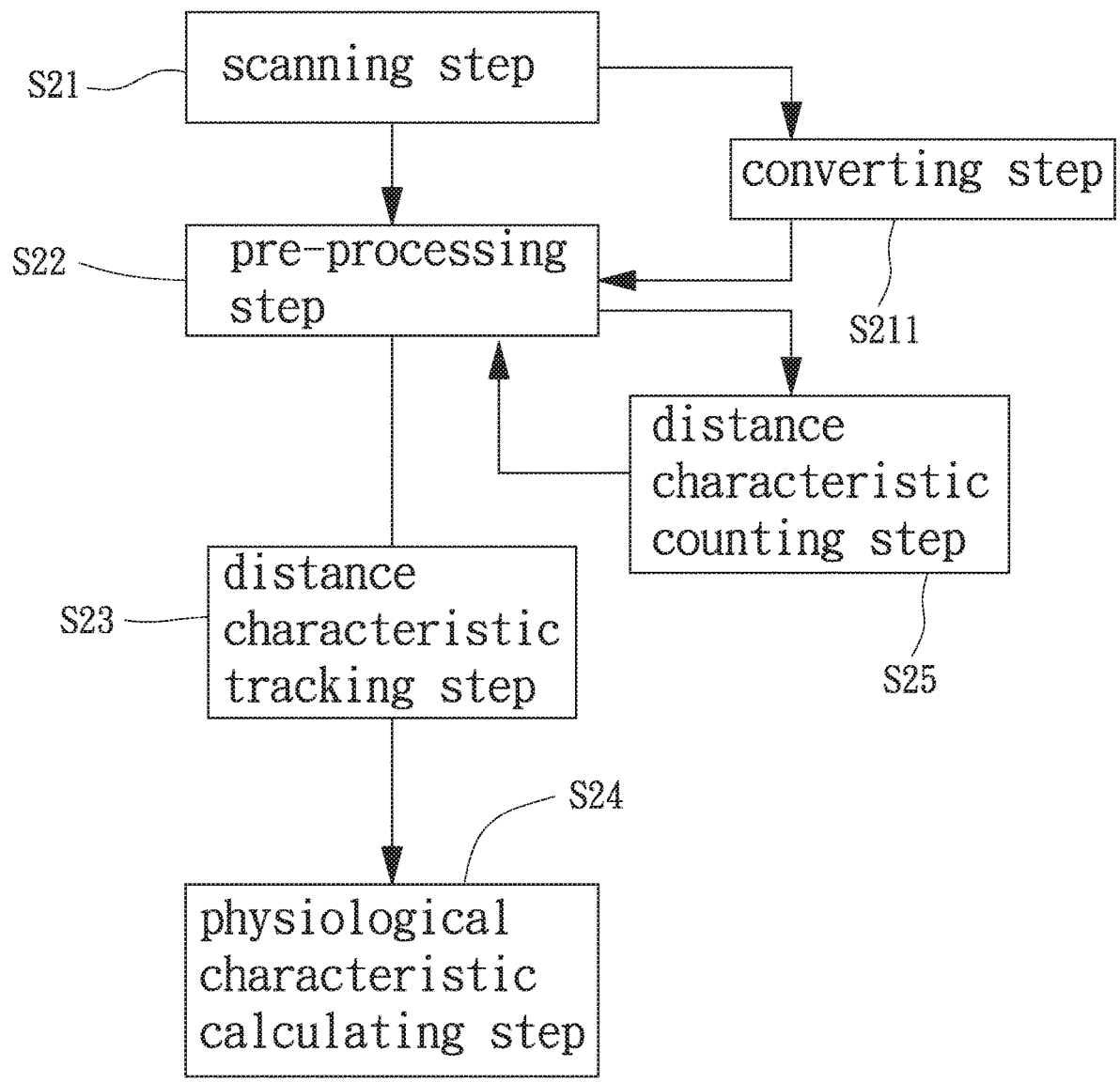
FIG. 3 is a method flow chart of a second embodiment of the present invention.

Referring to FIG. 3, a second embodiment of the non-contact method of physiological characteristic detection of the invention comprises a scanning step S21, a pre-processing step S22, a distance characteristic tracking step S23 and a physiological characteristic calculating step S24.

The scanning step S21 is configured to transmit a radar signal to at least one detected object (such as a person or an animal) through radar to obtain a reflected signal lasting for at least one time session. The number of the radar is not limited in the invention. In the embodiment, the number of the radar is described as one. The reflected signal can be a single signal or a mixed signal. In this embodiment, the radar signal transmitted by the radar can be a frequency modulated continuous wave (FMCW). The frequency modulation can be carried out with a triangular wave, a saw tooth wave, or by way of coded frequency modulation or noise frequency modulation, but is not limited thereto.

Specifically, the radar can continuously transmit a radar signal of a detection time to the detected object, and the detection time can include the at least one time session. When the at least one time session includes a plurality of time sessions, the time sessions can be sequentially divided into a first time session, a second time session, a third time session, etc. The length of each time session can be equal or unequal, which is not taken as a limited sense. In this embodiment, the detection time can be set to 30 seconds, in which the first time session can be set to 1-15 seconds and the second time session can be set to 2-16 seconds or 3-17 seconds. When the second time session is set to 2-16 seconds, the third time session can be set to 3-30 seconds. The frequency of the radar signal can be an electromagnetic wave of 2.45 GHz in the S band. It is worth mentioning that when the radar scans the detected object, the detected object preferably remains in the same motion state such that the reflected signal does not change greatly, thereby improving the accuracy of signal judgment.

The pre-processing step S22 is configured to perform a pre-processing procedure on the reflected signal, the pre-processing procedure is to set an estimated frequency for the time session to obtain a distance characteristic (such as frequency or phase) of each of the at least one detected object. Specifically, the estimated frequency can be any frequency in the fundamental frequency band corresponding to a distance characteristic signal, or can be obtained by performing a converting step S211. The range of the fundamental frequency band corresponding to the distance characteristic signal can be set according to a distance range to be measured by the radar. For example, when the distance range is 100-200 cm, the range of the fundamental frequency band can be 100 Hz-200 Hz, which can be understood by those with ordinary skill in the art.

The converting step S211 is configured to convert the reflected signal to the frequency domain through discrete Fourier transform (DFT) or fast Fourier transform (FFT) to generate spectrum information of the reflected signal. The pre-processing procedure can take the frequency having a maximum peak value in the spectrum information as the first estimated frequency. The pre-processing procedure obtains the energy of the wave corresponding to the estimated frequency. The wave can be a sinusoidal wave, a square wave or a triangular wave, which is not taken in a limited sense. The pre-processing step S22 is performed through an optimized algorithm to converge the wave energy with respect to the reflected signal to obtain a distance characteristic. In this embodiment, the optimized algorithm can be gradient descent method or Newton method.

It is worth mentioning that when the number of the at least one detected object is one and the number of the at least one time session is also one, the pre-processing step S22 can select any frequency from the fundamental frequency band as the estimated frequency. Further, when the number of the at least one detected object is one and the number of the at least one time session is plural, the pre-processing step S22 can arbitrarily select at least one time session in the plural time sessions, and take any frequency in the fundamental frequency band as the estimated frequency of the detected object in the time session. Furthermore, when the number of the at least one detected object is plural and the number of the at least one time session is one, the pre-processing step S22 can arbitrarily select at least one detected object in the plural detected objects, and take any frequency in the fundamental frequency band as the estimated frequency of the detected object. Moreover, when the number of the at least one detected object is plural and the number of the at least one time session is also plural, the pre-processing step S22 can arbitrarily select at least one time session in the plural time sessions, arbitrarily select at least one detected object in the plural detected objects in the time session, and take any frequency in the fundamental frequency band as the estimated frequency of the detected object. Thus, in the calculating process of obtaining the distance characteristic, the invention does not need to perform Fourier transform calculations, or can reduce at least one round of Fourier transform calculations, which has the functions of reducing the calculation complexity and improving the operational efficiency.

The distance characteristic tracking step S23 is configured to track the distance characteristic of the detected object in the time session, and to obtain a distance change function of the detected object according to the change of the distance characteristic in each time session (for example, frequency change or phase change corresponding to the frequency change in the spectrum information). For example, when the number of the at least one time session is plural, the distance characteristics of the distance change function of each of the at least one detected object in the plural time sessions are taken that the distance characteristic(s) obtained in a first time session of the plural time sessions is used as the estimated frequency of a second time session of the plural time sessions succeeding the first time session. That is, the distance characteristic of the previous time session is taken as the estimated frequency of the next time session. In this way, the distance change function can be generated according to the change of the distance characteristic in each time session.

On the other hand, when the distance characteristics of the plural detected objects are obtained in the first time session and the second time session, the distance characteristic tracking step S23, in addition to using the above method to generate the distance change function of the plural detected objects in each time session, can also sort the energy (or energies) of the distance characteristic (or characteristics) calculated in each time session. In this regard, the distance characteristic tracking step S23 sequentially picks a number of the distance characteristic(s) equal to the number of the at least one detected object by way of energy selection from large to small, and takes the distance characteristics with the same order in the time sessions as the distance characteristics of the same detected object. Then, the distance change function can be generated according to the change of the distance characteristic in each time session. For example, the distance characteristics having the maximum energy in the first time session and the second time session are distance characteristics of one of the plural detected objects; the distance characteristics having the second largest energy in the first time session and the second time session are distance characteristics of the other detected object, and so on.

The physiological characteristic calculating step S24 is configured to convert the distance change function to the frequency domain to generate spectrum information of the distance change function, and to obtain a physiological characteristic of the detected object according to the spectrum information. Specifically, the physiological characteristic calculating step S24 can convert the distance change function to frequency domain through discrete Fourier transform (DFT) or fast Fourier transform (FFT), thereby generating the spectrum information of the distance change function. The physiological characteristic calculating step S24 can take the frequency of the spectrum information having a maximum peak value as the physiological characteristic of the detected object.

When the number of the at least one detected object is plural, the second embodiment of the non-contact method of physiological characteristic detection of the invention can further include a distance characteristic counting step S25. The distance characteristic counting step S25 is configured to determine whether the number of the distance characteristic(s) obtained in each time session is less than the number of the at least one detected object. If the determined result is yes, the signal difference between the reflected signal and the wave corresponding to the distance characteristic can be calculated to generate a residual signal. In this regard, a frequency can be selected from the fundamental frequency band as the estimated frequency, or the frequency having the maximum peak value in the spectrum information of the residual signal can be used as the estimated frequency. The pre-processing step S22 uses the optimized algorithm to converge the wave energy of the estimated frequency with respect to the residual signal to obtain a distance characteristic of another detected object. If the determined result is no, it means that the number of the distance characteristic(s) that meets the distance characteristic(s) of the at least one detected object has been obtained, then the distance characteristic counting step S25 can be stopped.

According to the method of the second embodiment, when the non-contact method of physiological characteristic detection of the invention is applied, the radar can be designed to correspond to an actual distance of 1 cm per Hz, and the range of the distance to be detected by the radar is 100-200 cm. Therefore, in the embodiment, the estimated frequency can be set to 150 Hz. When two subjects are simultaneously detected, it is assumed that the reflected signal contains distance characteristic signals of 130 Hz and 170 Hz. Since the energy intensity corresponding to the distance characteristic of 130 Hz is larger, when the optimized algorithm is performed on the estimated frequency, the energy of the wave corresponding to the estimated frequency will gradually converge toward 130 Hz to obtain the distance characteristic of 130 Hz for one of the two subjects. Since the number of the distance characteristics currently obtained is less than the number of the subjects, the estimated frequency is reset and a signal difference between the reflected signal and the wave corresponding to the distance characteristic is calculated to generate a residual signal. Assuming that the estimated frequency is still set to 150 Hz, the energy of the wave corresponding to the estimated frequency will gradually converge toward 170 Hz after performing the optimized algorithm on the estimated frequency, so as to obtain the distance characteristic of 170 Hz for the other of the two subjects. Then, if it is necessary to detect and obtain the distance characteristics of the two subjects in the next time session, 130 Hz and 170 Hz can be respectively taken as the estimated frequencies of the next time session to obtain the distance characteristics of the two subjects in the next time session.

Figure 4:
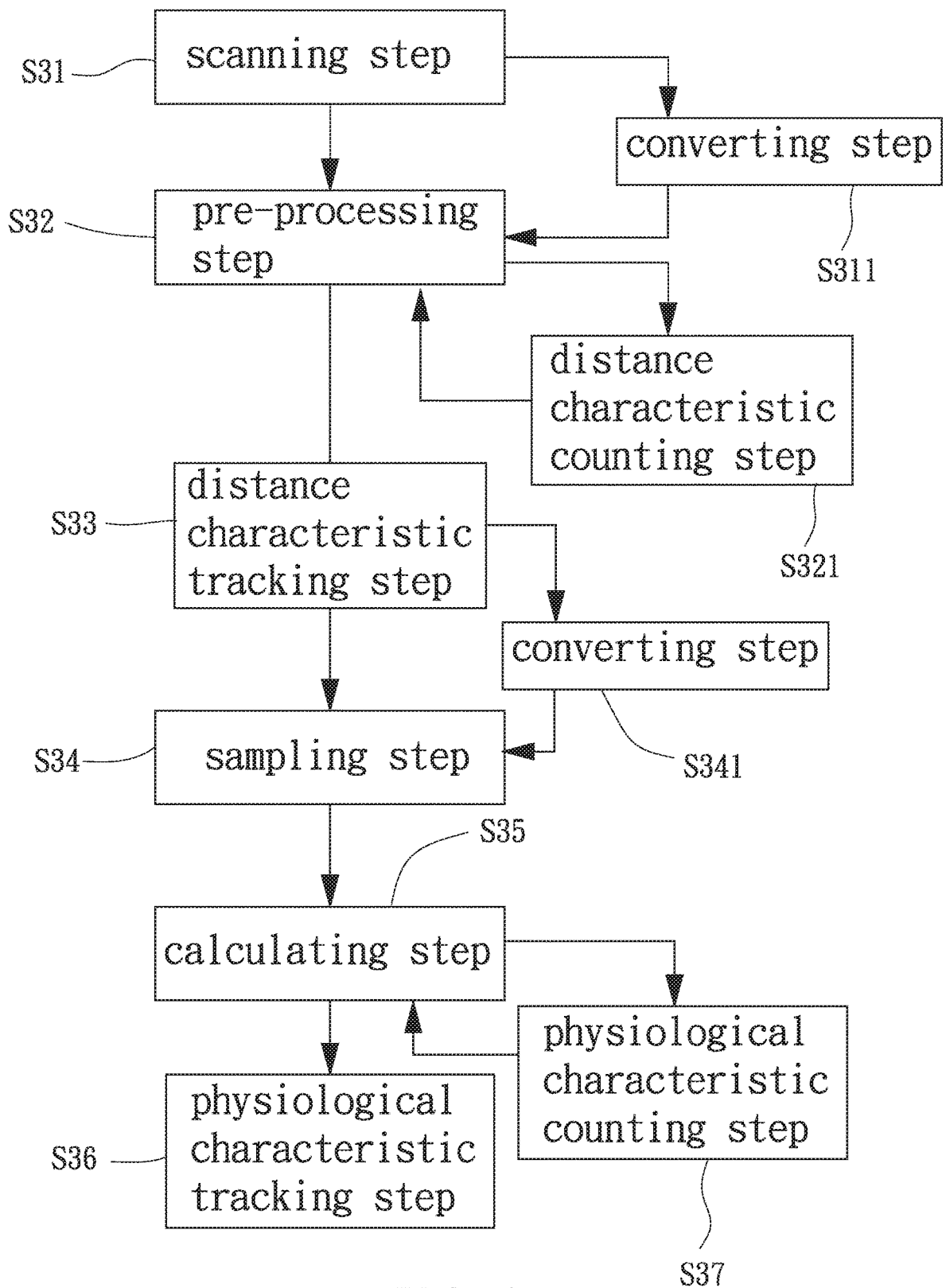
FIG. 4 is a method flow chart of a third embodiment of the present invention.

Referring to FIG. 4, a third embodiment of the non-contact method of physiological characteristic detection of the invention includes a scanning step S31, a pre-processing step S32, a distance characteristic tracking step S33, a sampling step S34 and a calculating step S35.

The scanning step S31 is configured to transmit a radar signal to at least one detected object (such as a person or an animal) through radar to obtain a reflected signal lasting for at least one time session, and the number of the radar(s) is not limited in the invention. In the embodiment, the number of the radar is described as one. The reflected signal can be a single signal or a mixed signal. In this embodiment, the radar signal transmitted by the radar can be a frequency modulated continuous wave (FMCW). The frequency modulation can be carried out with a triangular wave, a saw tooth wave, or by way of coded frequency modulation or noise frequency modulation, but is not limited thereto.

Specifically, the radar may continuously transmit a radar signal for a period of detection time to the detected object, and the detection time can include the at least one time session. When the at least one time session includes a plurality of time sessions, the time sessions can be sequentially divided into a first time session, a second time session, a third time session, etc. The length of each time session can be equal or unequal, which is not taken as a limited sense. In this embodiment, the detection time can be set to 30 seconds, in which the first time session can be set to 1-15 seconds and the second time session can be set to 2-16 seconds or 3-17 seconds. When the second time session is set to 2-16 seconds, the third time session can be set to 3-30 seconds. The frequency of the radar signal can be an electromagnetic wave of 2.45 GHz in the S band. It is worth mentioning that when the radar scans the detected object, the detected object preferably remains in the same motion state such that the reflected signal does not change greatly, thereby improving the accuracy of signal judgment.

The pre-processing step S32 is configured to perform a pre-processing procedure on the reflected signal, and the pre-processing procedure is to set a first estimated frequency for the time session to obtain a distance characteristic (such as frequency or phase) of each of the at least one detected object. Specifically, the first estimated frequency can be any frequency in the fundamental frequency band corresponding to a distance characteristic signal, or can be obtained by performing a converting step S311. The range of the fundamental frequency band corresponding to the distance characteristic signal can be set according to a distance range to be measured by the radar. For example, when the distance range is 100-200 cm, the fundamental frequency band can be 100 Hz-200 Hz, which can be understood by those with ordinary skill in the art.

The converting step S311 is configured to convert the reflected signal to the frequency domain through discrete Fourier transform (DFT) or fast Fourier transform (FFT) to generate spectrum information of the reflected signal. The pre-processing procedure can take the frequency having a maximum peak value in the spectrum information as the first estimated frequency. The pre-processing procedure obtains the energy of the wave corresponding to the first estimated frequency. The wave can be a sinusoidal wave, a square wave or a triangular wave, but is not limited thereto. The pre-processing step S32 is performed through an optimized algorithm to converge the wave energy with respect to the reflected signal to obtain a distance characteristic. In this embodiment, the optimized algorithm can be gradient descent method or Newton method.

It is worth mentioning that when the number of the at least one detected object is one and the number of the at least one time session is also one, the pre-processing step S32 can select any frequency in the fundamental frequency band as the first estimated frequency. Further, when the number of the at least one detected object is one and the number of the at least one time session is plural, the pre-processing step S32 arbitrarily selects at least one time session in the plural time sessions, and takes any frequency in the fundamental frequency band as a first estimated frequency of the detected object in the time session. Furthermore, when the number of the at least one detected object is plural and the number of the at least one time session is one, the pre-processing step S32 arbitrarily selects at least one detected object in the plural detected objects, and takes any frequency in the fundamental frequency band as the first estimated frequency of the detected object. Moreover, when the number of the at least one detected object is plural and the number of the at least one time session is also plural, the pre-processing step S32 can arbitrarily select at least one time session in the plural time sessions, arbitrarily select at least one detected object in the plural detected objects in the time session, and take any frequency in the fundamental frequency band as the first estimated frequency of the detected object. In this way, the invention does not need to perform Fourier transform calculations in the calculating process of obtaining the distance characteristic, or can reduce at least one round of Fourier transform calculations, which has the functions of reducing the calculation complexity and improving the operational efficiency.

Preferably, when the number of the at least one detected object is plural, the pre-processing step S32 can further perform a distance characteristic counting step S321 configured to determine whether the number of the distance characteristics obtained in each time session is less than the number of the at least one detected object. If the determined result is yes, the signal difference between the reflected signal and the wave corresponding to the distance characteristic can be calculated to generate a residual signal. In this regard, a frequency in the fundamental frequency band is selected as the first estimated frequency, or the frequency having the maximum peak value in the spectrum information of the residual signal is selected as the first estimated frequency. The pre-processing step S32 uses the optimized algorithm to converge the wave energy of the first estimated frequency with respect to the residual signal, so as to obtain a distance characteristic of another detected object. If the determined result is no, it means that the number of the distance characteristic(s) that meets the distance characteristic(s) of the at least one detected object has been obtained, then the distance characteristic counting step S321 can be stopped.

The distance characteristic tracking step S33 is configured to track the distance characteristic of the detected object in the time session, and to obtain a distance change function of the detected object according to the change of the distance characteristic in each time session (for example, frequency change or phase change corresponding to the frequency change in the spectrum information). For example, when the number of the at least one time session is plural, the distance characteristics of the distance change function of each of the at least one detected object in the plural time sessions are taken that the distance characteristic(s) obtained in a first time session of the plural time sessions is used as the first estimated frequency of a second time session of the plural time sessions succeeding the first time session. That is, the distance characteristic of the previous time session is taken as the first estimated frequency of the next time session. In this way, the distance change function can be generated according to the change of the distance characteristic in each time session.

On the other hand, when the distance characteristics of the plural detected objects are obtained in the first time session and the second time session, the distance characteristic tracking step S33, in addition to using the above method to generate the distance change function of the plural detected objects in each time session, can also sort the energy (or energies) of the distance characteristic (or characteristics) calculated in each time session. In this regard, the distance characteristic tracking step S33 sequentially picks a number of the distance characteristic(s) equal to a number of the at least one detected object by way of energy selection from large to small, and takes the distance characteristics with the same order in the time sessions as the distance characteristics of the same detected object. Then, the distance change function can be generated according to the change of the distance characteristic in each time session. For example, the distance characteristics having the maximum energy in the first time session and the second time session are distance characteristics of one of the plural detected objects; the distance characteristics having the second largest energy in the first time session and the second time session are distance characteristics of the other detected object, and so on.

The sampling step S34 is configured to set a second estimated frequency for the time session. Specifically, the second estimated frequency can be any frequency in the fundamental frequency band corresponding to a physiological characteristic signal, or can be obtained by performing a converting step S341. Specifically, when the physiological characteristic signal is a respiratory signal, the estimated frequency is preferably set to any frequency in the fundamental frequency band, which is, for example, 0.5 Hz, as it can be understood by those with ordinary skill in the art. The converting step S341 can convert the distance change function to the frequency domain through discrete Fourier transform (DFT) or fast Fourier transform (FFT) to generate spectrum information of the distance change function. The sampling step S34 can take the frequency having a maximum peak value in the spectrum information as the second estimated frequency.

It is worth mentioning that when the number of the at least one detected object is one and the number of the at least one time session is also one, the sampling step S34 can select any frequency in the fundamental frequency band as the second estimated frequency. Further, when the number of the at least one detected object is one and the number of the at least one time session is plural, the sampling step S34 arbitrarily selects at least one time session in the plural time sessions, and takes any frequency in the fundamental frequency band as the second estimated frequency of the detected object in the time session. Furthermore, when the number of the at least one detected object is plural and the number of the at least one time session is one, the sampling step S34 arbitrarily selects at least one detected object in the plural detected objects, and takes any frequency in the fundamental frequency band as the second estimated frequency of the detected object. Moreover, when the number of the at least one detected object is plural and the number of the at least one time session is also plural, the sampling step S34 can select at least one time session in the plural time sessions, select at least one detected object in the plural detected objects in the time session, and take any frequency in the fundamental frequency band as the second estimated frequency of the detected object. In this way, the invention does not need to perform Fourier transform calculations in the calculation process of detecting the physiological characteristics, or can reduce at least one round of Fourier transform calculations, which has the functions of reducing the calculation complexity and improving the operational efficiency.

The calculating step S35 is configured to obtain the energy of the wave corresponding to the second estimated frequency, and the wave can be a sinusoidal wave, a square wave or a triangular wave, but is not limited thereto. The calculating step S35 is performed by an optimized algorithm to converge the wave energy with respect to the distance change function, which is to optimize the wave energy to minimize the energy difference corresponding to the distance change function, so as to obtain a physiological characteristic of the detected object. In this embodiment, the optimized algorithm can be gradient descent method or Newton method.

The third embodiment of the non-contact method of physiological characteristic detection of the invention can further include a physiological characteristic tracking step S36, which is configured to track the physiological characteristics of the plural detected objects in each time session. For example, when the number of the at least one time session is plural, the physiological characteristics acquired in a first time session of the plural time sessions can be used as a second estimated frequency of a second time session of the plural time sessions succeeding the first time session. That is, the physiological characteristic of the previous time session is used as the second estimated frequency of the next time session. Specifically, when the physiological characteristics of the detected object is acquired in the second time session, the sampling step S34 can take the physiological characteristics calculated in the first time session as the second estimated frequency of the second time session. The calculating step S35 obtains the energy of the wave corresponding to the second estimated frequency of the second time session, and converges the wave energy with respect to the distance change function of the second time session through the optimized algorithm, so as to minimize the energy difference between the wave energy corresponding to the estimated frequency and the reflected signal to obtain the physiological characteristic of the detected object in the second time session.

On the other hand, when the physiological characteristics of the plural detected objects are obtained in the first time session and the second time session, the physiological characteristic tracking step S36, in addition to using the above method to track the physiological characteristics of the plural detected objects in each time session, can also track the physiological characteristics of the plural detected objects in each time session by sorting the energy intensities corresponding to the physiological characteristics obtained in the first time session and the second time session. The energy intensities can be sorted from large to small or from small to large, but it is not the limitation of the invention.

Specifically, the physiological characteristic tracking step S36 can perform energy sorting on the calculated physiological characteristics in each time session, and sequentially select the physiological characteristics equivalent to the number of the at least one detected object by way of energy selection from large to small. In this regard, the physiological characteristics having the same sorting order in each time session are taken as the physiological characteristics of the same detected object. For example, the physiological characteristics having the maximum energy in the first time session and the second time session are physiological characteristics of one of the plural detected objects; the physiological characteristics having the second largest energy in the first time session and the second time session are physiological characteristics of another detected object, and so on.

When the number of the at least one detected object is plural, the third embodiment of the non-contact method of physiological characteristic detection of the invention can further include a physiological characteristic counting step S37 configured to determine whether the number of the physiological characteristic obtained in each time session is less than the number of the at least one detected object. If the determined result is yes, the signal difference between the distance change function and the wave corresponding to the physiological characteristic can be calculated to generate a residual signal. In this regard, a frequency can be selected from the fundamental frequency band as the estimated frequency, or the frequency having the maximum peak value can be selected from the spectrum information of the residual signal as the second estimated frequency. If the determined result is no, it means that the number of the physiological characteristic(s) that meets the physiological characteristic(s) of the at least one detected object has been obtained, then the physiological characteristic counting step S37 can be stopped.

In conclusion, the non-contact method of physiological characteristic detection of the invention is capable of converging the wave energy of the set estimated frequency relative to the reflected signal of the radar through the optimized algorithm, so as to obtain the physiological characteristic of the subject. Thus, the non-contact method of physiological characteristic detection of the invention can reflect the change of the physiological characteristic of the subject in a short time without being affected by the frequency resolution, thereby improving the accuracy in detecting the physiological characteristics.

Although the invention has been described in detail with reference to its presently preferable embodiments, it will be understood by one of ordinary skill in the art that various modifications can be made without departing from the spirit and the scope of the invention, as set forth in the appended claims.

What is claimed is:

1. A non-contact method of physiological characteristic detection, comprising:
    transmitting a radar signal to at least one detected object through a radar to obtain a reflected signal lasting for at least one time session;
    setting an estimated frequency for each of the at least one time session;
    obtaining a wave energy corresponding to the estimated frequency; and
    converging the wave energy with respect to the reflected signal through an optimized algorithm to obtain a physiological characteristic of each of the at least one detected object.

2. The non-contact method of physiological characteristic detection of claim 1, wherein the estimated frequency is any frequency in a fundamental frequency band corresponding to a physiological characteristic signal, or a frequency having a maximum peak value in spectrum information generated by converting the reflected signal to frequency domain.

3. The non-contact method of physiological characteristic detection of claim 2, wherein the at least one detected object includes a plurality of detected objects, wherein the method further comprises determining whether a number of the physiological characteristics obtained in each of the at least one time session is less than a number of the plurality of detected objects, wherein, if the determined result is positive, the method further comprises:
    calculating a signal difference between the reflected signal and a wave corresponding to the physiological characteristic to generate a residual signal;
    reselecting any frequency in the fundamental frequency band as the estimated frequency or selecting a frequency having a maximum peak value from the spectrum information of the residual signal as the estimated frequency; and
    performing an optimized algorithm to converge the wave energy of the estimated frequency relative to the residual signal to obtain the physiological characteristic of another of the plurality of detected objects.

4. The non-contact method of physiological characteristic detection of claim 1, wherein the at least one time session includes a plurality of time sessions, and wherein the physiological characteristic obtained in a first time session of the plurality of time sessions is taken as the estimated frequency of a second time session of the plurality of time sessions succeeding the first time session.

5. The non-contact method of physiological characteristic detection of claim 1, wherein the at least one time session includes a plurality of time sessions, wherein the physiological characteristic(s) of the at least one detected object calculated in each of the plurality of time sessions is sorted by energy, wherein the physiological characteristic(s) equal to a number of the at least one detected object is selected in order by way of energy selection from large to small, and wherein the physiological characteristics with a same order in the plurality of time sessions are taken as the physiological characteristics of a same one of the at least one detected object.

6. A non-contact method of physiological characteristic detection, comprising:
    transmitting a radar signal to at least one detected object through a radar to obtain a reflected signal lasting for at least one time session;
    performing a pre-processing procedure on the reflected signal, the pre-processing procedure being configured to set an estimated frequency for each of the at least one time session to obtain a wave energy corresponding to the estimated frequency;
    making the wave energy converge with respect to the reflected signal through an optimized algorithm to obtain a distance characteristic of each of the at least one detected object;
    tracking the distance characteristic of each of the at least one detected object in the at least one time session;

obtaining a distance change function of each of the at least one detected object according to a change of the distance characteristic in each of the at least one time session;

converting the distance change function to the frequency domain to generate spectrum information of the distance change function; and obtaining a physiological characteristic of each of the at least one detected object according to the spectrum information.

7. The non-contact method of physiological characteristic detection of claim 6, wherein the estimated frequency is any frequency in a fundamental frequency band corresponding to a distance characteristic signal, or a frequency having a maximum peak value in the spectrum information generated by converting the reflected signal to the frequency domain.

8. The non-contact method of physiological characteristic detection of claim 7, wherein the at least one detected object includes a plurality of detected objects, wherein the method further comprises determining whether a number of the distance characteristic(s) obtained in each of the at least one time session is less than a number of the plurality of detected objects, wherein, if the determined result is positive, the method further comprises:

calculating a signal difference between the reflected signal and a wave corresponding to the distance characteristic to generate a residual signal;

reselecting any frequency in the fundamental frequency band as the estimated frequency or selecting a frequency having a maximum peak value from the spectrum information of the residual signal as the estimated frequency;

performing the optimized algorithm to converge the wave energy of the estimated frequency relative to the residual signal to obtain the distance characteristic of another of the plurality of detected objects; and obtaining the physiological characteristic of the other of the plurality of detected objects according to the distance characteristic.

9. The non-contact method of physiological characteristic detection of claim 6, wherein the at least one time session includes a plurality of time sessions, and wherein the distance characteristic of the distance change function of each of the at least one detected object in a first time session of the plurality of time sessions is taken as the estimated frequency of a second time session of the plurality of time sessions succeeding the first time session.

10. The non-contact method of physiological characteristic detection of claim 6, wherein the at least one time session includes a plurality of time sessions, wherein the distance characteristic(s) calculated in each of the plurality of time sessions is sorted by energy, wherein the distance characteristic(s) equal to a number of the at least one detected object is selected in order by way of energy selection from large to small, and wherein the distance characteristics with a same order in the plurality of time sessions are taken as the distance characteristics of a same one of the at least one detected object to thereby generate the distance change function of the same one of the at least one detected object in the plurality of time sessions.

11. A non-contact method of physiological characteristic detection, comprising:

transmitting a radar signal to at least one detected object through a radar to obtain a reflected signal lasting for at least one time session;

performing a pre-processing procedure on the reflected signal, the pre-processing procedure being configured to set a first estimated frequency for each of the at least one time session to obtain a wave energy corresponding to the first estimated frequency;

making the wave energy converge with respect to the reflected signal through an optimized algorithm to obtain a distance characteristic of each of the at least one detected object;

tracking the distance characteristic of each of the at least one detected object in the at least one time session;

obtaining a distance change function of each of the at least one detected object according to a change of the distance characteristic in each of the at least one time session;

setting a second estimated frequency for each of the at least one time session to obtain a wave energy corresponding to the second estimated frequency; and making the wave energy of the second estimated frequency converge relative to the distance change function through the optimized algorithm to obtain a physiological characteristic of each of the at least one detected object.

12. The non-contact method of physiological characteristic detection of claim 11, wherein the first estimated frequency is any frequency in a fundamental frequency band corresponding to a distance characteristic signal, or a frequency having a maximum peak value in spectrum information generated by converting the reflected signal to the frequency domain.

13. The non-contact method of physiological characteristic detection of claim 12, wherein the at least one detected object includes a plurality of detected objects, wherein the method further comprises determining whether a number of the distance characteristic obtained in each of the at least one time session is less than a number of the plurality of detected objects, wherein, if the determined result is positive, the method further comprises:

calculating a signal difference between the reflected signal and a wave corresponding to the distance characteristic to generate a residual signal;

reselecting any frequency in the fundamental frequency band as the estimated frequency or selecting a frequency having a maximum peak value from the spectrum information of the residual signal as the first estimated frequency;

performing the optimized algorithm to converge the wave energy of the first estimated frequency relative to the residual signal to obtain a distance characteristic of another of the plurality of detected objects; and obtaining the physiological characteristic of the other of the plurality of detected objects according to the distance characteristic.

14. The non-contact method of physiological characteristic detection of claim 11, wherein the second estimated frequency is any frequency in a fundamental frequency band corresponding to a physiological characteristic signal, or a frequency having a maximum peak value in spectrum information generated by converting the distance change function to the frequency domain.

15. The non-contact method of physiological characteristic detection of claim 14, wherein the at least one detected object includes a plurality of detected objects, wherein the method further comprises determining whether a number of the physiological characteristic obtained in each of the at least one time session is less than a number of the plurality of detected objects, wherein, if the determined result is positive, the method further comprises:

calculating a signal difference between the distance change function and a wave corresponding to the physiological characteristic to generate a residual signal;

reselecting any frequency in the fundamental frequency band as the estimated frequency or selecting a frequency having a maximum peak value from the spectrum information of the residual signal as the second estimated frequency; and performing the optimized algorithm to converge the wave energy of the second estimated frequency relative to the residual signal to obtain the physiological characteristic of another of the plurality of detected objects.

16. The non-contact method of physiological characteristic detection of claim 11, wherein the at least one time session includes a plurality of time sessions, and wherein the distance characteristic of the distance change function of each of the at least one detected object in a first time session of the plurality of time sessions is taken as the first estimated frequency of a second time session of the plurality of time sessions succeeding the first time session.

17. The non-contact method of physiological characteristic detection of claim 11, wherein the at least one time session includes a plurality of time sessions, wherein the distance characteristic(s) calculated in each of the plurality of time sessions is sorted by energy, wherein the distance characteristics equal to a number of the at least one detected object is selected in order by way of energy selection from large to small, and wherein the distance characteristics with a same order in the plurality of time sessions are taken as the distance characteristics of a same one of the at least one detected object to thereby generate the distance change function of the same one of the at least one detected object in the plurality of time sessions.

18. The non-contact method of physiological characteristic detection of claim 11, wherein the at least one time session includes a plurality of time sessions, wherein the physiological characteristic obtained in a first time session of the plurality of time sessions is taken as the second estimated frequency of a second time session of the plurality of time sessions succeeding the first time session.

19. The non-contact method of physiological characteristic detection of claim 11, wherein the at least one time session includes a plurality of time sessions, wherein the physiological characteristic(s) calculated in each of the plurality of time sessions is sorted by energy, wherein the physiological characteristic(s) equal to a number of the at least one detected object is selected in order by way of energy selection from large to small, and wherein the physiological characteristics with a same order in the plurality of time sessions are taken as the physiological characteristics of a same one of the at least one detected object.

* * * * *